US00PP31277P2

(12) United States Plant Patent
Hartman

(10) Patent No.: US PP31,277 P2
(45) Date of Patent: Dec. 24, 2019

(54) ***CALADIUM* PLANT NAMED 'WWG 2320-373'**

(50) Latin Name: ***Caladium* X *hortulanum***
Varietal Denomination: WWG 2320-373

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/350,103

(22) Filed: Sep. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1
CPC ... A01H 5/12; A01H 5/00; A01H 5/02; A01H 6/00
See application file for complete search history.

*Primary Examiner* — June Hwu
(74) *Attorney, Agent, or Firm* — C. A. Whealy

(57) ABSTRACT

A new and distinct cultivar of *Caladium* plant named 'WWG 2320-373', characterized by its short to intermediate height; upright and mounding plant habit; dense and bushy appearance; vigorous growth habit and rapid growth rate; lance-type leaves that are medium to dark green in color with bright white-colored centers and light green-colored venation; and petioles that are medium green in color with darker-colored stipples, streaks and tessellations.

4 Drawing Sheets

Botanical designation: *Caladium* X *hortulanum*.
Cultivar denomination: 'WWG 2320-373'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'WWG 2320-373'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'Florida Sweetheart', disclosed in U.S. Plant Pat. No. 8,526, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WWG 2320-373'. These characteristics in combination distinguish 'WWG 2320-373' as a new and distinct *Caladium* plant:

1. Short to intermediate in height and upright and mounding plant habit; dense and bushy appearance.
2. Vigorous growth habit and rapid growth rate.
3. Lance-type leaves that are medium to dark green in color with bright white-colored centers and light green-colored venation.
4. Petioles that are medium green in color with darker-colored stipples, streaks and tessellations.

Plants of the new *Caladium* differ primarily from plants of the female parent, 'Florida Sweetheart', in the following characteristics:

1. Plants of the new *Caladium* grow faster than plants of 'Florida Sweetheart'.
2. Plants of the new *Caladium* and 'Florida Sweetheart' differ in leaf color as leaves of the new *Caladium* are medium to dark green in color with bright white-colored centers and light green-colored venation whereas leaves of 'Florida Sweetheart' have dark pink-colored venation, rose pink-colored interveinal areas with greenish white-colored margins.
3. Plants of the new *Caladium* and 'Florida Sweetheart' differ in leaf petiole color as petioles of the new *Caladium* are medium green in color with darker-colored stipples, streaks and tessellations whereas petioles of 'Florida Sweetheart' are pinkish tan with darker-colored stripes.

Plants of the new *Caladium* differ primarily from plants of the male parent, 'White Wonder', in the following characteristics:

1. Plants of the new *Caladium* more mounding than and not as upright as plants of 'White Wonder'.
2. Plants of the new *Caladium* and 'White Wonder' differ in leaf color as leaves of the new *Caladium* are medium to dark green in color with bright white-colored centers and light green-colored venation whereas leaves of 'White Wonder' are white to grey-green in color with light pink to white-colored venation and dark green-colored borders.
3. Plants of the new *Caladium* and 'White Wonder' differ in leaf petiole color as petioles of the new *Caladium* are medium green in color with darker-colored stipples, streaks and tessellations whereas petioles of 'White Wonder' are greenish tan with darker-colored stripes.

Plants of the new *Caladium* can be compared to plants of *Caladium* X *hortulanum* 'White Dynasty', disclosed in U.S. Plant Pat. No. 22,240. In side-by-side comparisons, plants of the new *Caladium* differ primarily from plants of 'White Dynasty' in the following characteristics:

1. Plants of the new *Caladium* grow faster than plants of 'White Dynasty'.
2. Plants of the new *Caladium* and 'White Dynasty' differ in leaf color as leaves of the new *Caladium* are medium to dark green in color with bright white-colored centers and light green-colored venation whereas leaves of 'White Dynasty' are white and greyed green with few random red purple-colored spots, dark green-colored margins and greyed green-colored venation.
3. Plants of the new *Caladium* and 'White Dynasty' differ in leaf petiole color as petioles of the new *Caladium* are medium green in color with darker-colored stipples, streaks and tessellations whereas petioles of 'White Dynasty' are darker green in color and tinged with brownish green.

Plants of the new *Caladium* can be compared to plants of *Caladium* X *hortulanum* 'RS-03-03', disclosed in U.S. Plant Pat. No. 26,265. In side-by-side comparisons, plants of the new *Caladium* differ primarily from plants of 'RS-03-03' in the following characteristics:

1. Leaves of plants of the new *Caladium* are broader and wavier than and not as narrow and flat as leaves of plants of 'RS-03-03'.
2. Plants of the new *Caladium* and 'RS-03-03' differ in leaf color as leaves of the new *Caladium* are medium to dark green in color with bright white-colored centers and light green-colored venation whereas leaves of 'RS-03-03' are pearlescent white to greenish white in color with dark green-colored margins and white to greenish white-colored venation.
3. Plants of the new *Caladium* and 'RS-03-03' differ in leaf petiole color as petioles of the new *Caladium* are medium green in color with darker-colored stipples, streaks and tessellations whereas petioles of 'RS-03-03' are darker green in color and tinged with brown.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'WWG 2320-373' in a container and grown in a shadehouse (tuber de-eyed).

The photograph at the top of the second sheet is a comparison view of typical potted plants of the female parent, 'Florida Sweetheart' (left), 'WWG 2320-373' (center) and the male parent, 'White Wonder' (right).

The photograph at the bottom of the second sheet is a comparison view of typical potted plants of 'White Dynasty' (left), 'WWG 2320-373' (center) and 'RS-03-03' (right).

The photograph at the top of the third sheet is a comparison view of typical plants of 'WWG 2320-373' grown in containers; the plant on the left has not had its tuber de-eyed and the plant on the right has had its tuber de-eyed prior to planting.

The photograph at the bottom of the third sheet is a close-up view of typical freshly-harvested tubers with roots and leaf petioles of 'WWG 2320-373'.

The photograph at the top of the fourth sheet is a side perspective view of typical plants of 'WWG 2320-373' grown in an open production field.

The photograph at the bottom of the fourth sheet is a close-up view of a typical inflorescence of 'WWG 2320-373'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were twelve weeks old and plants grown in the outdoor nursery were 7.5 months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'WWG 2320-373'.

Parentage:

*Female, or seed, parent.*—*Caladium* X *hortulanum* 'Florida Sweetheart', disclosed in U.S. Plant Pat. No. 8,526.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular to ovate in shape. Height: About 4.1 cm. Diameter: About 6.8 cm to 8.5 cm. Segment height: About 2.6 cm to 3.4 cm. Segment diameter: About 2.5 cm to 3 cm. Axillary bud size: About 4 mm by 6 mm. Texture: Thick, starchy; somewhat brittle. Color: Epidermis, freshly-harvested: Lighter than 182D. Epidermis, dried: Close to 200A. Cortical tissue: Close to 4D. Axillary buds: Close to 38C and 38D. Root description: Thick, fleshy contractile roots with few lateral branches; color, close to 155C faintly tinged with close to 182D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Short to intermediate in height and upright to mounded plant habit; dense and bushy appearance; vigorous growth habit and rapid growth rate; potted plants finish in saleable form in about seven weeks after planting tubers; leaf petioles and leaves arise from one or more growing points on tubers; leaf petioles initially upright and outwardly leaning to arching with development.

*Plant height, from soil level to top of foliar plane, shadehouse-grown potted plants*.—About 23 cm to 29 cm.

*Plant height, from soil level to top of inflorescences, shadehouse-grown potted plants*.—About 25.2 cm.

*Plant diameter or spread, shadehouse-grown potted plants*.—About 44 cm to 48 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About four to five develop per #1 tuber.

*Cataphylls, shadehouse-grown potted plants*.—Length: About 4.7 cm. Width: About 1.2 cm. Shape: Lanceolate. Apex: Acuminate. Base: Sheathing the stem. Color, inner surface: Close to 155C; colors and patterns on the outer surface are visible on the inner surface. Color, outer surface: Close to 156D and 146D tinged with close to 199B, streaked and stippled with close to 200C; with development, color becoming closer to 200B.

Leaf description:

*Arrangement and type*.—Alternate; simple; lance-type.

*Length, shadehouse-grown potted plants*.—About 16 cm to 21 cm.

*Width, shadehouse-grown potted plants*.—About 8.5 cm to 13 cm; when flattened, about 10.8 cm to 14.5 cm.

*Shape*.—Ovate to lanceolate.

*Apex*.—Acute to acuminate.

*Base*.—Sagittate to peltate.

*Margin*.—Entire; wavy with broad undulations.

*Texture and luster, upper surface*.—Smooth, glabrous; dull sheen.

*Texture and luster, lower surface*.—Smooth, glabrous; slightly glaucous with a dull sheen.

*Venation pattern*.—Pinnate.

*Color, shadehouse-grown potted plants*.—Developing and fully developed leaves, upper surface: Background color: Close to 155C. Towards the margins: Close to 147A and 147B. Leaf edge: Narrow, close to 157D. Basal notch: Close to N186D. Leaf attachment point: Close to 183A. Midvein and primary venation: Close to 147D and 194D. Interveinal areas: Close to 157C, 157D and 194C with specks, close to 147A and 147B.

*Developing and fully developed leaves, lower surface*.—Background color: Close to 155C. Towards the margins: Close to 191A and close to 191A tinged with close to 189A. Leaf edge: Close to 157D. Basal notch: Close to N186C. Leaf attachment point: Close to N186D. Midvein: Close to 147C and 147D. Primary venation: Close to 147C and 146C. Lateral venation: Close to 147A, 147C and close to 147C tinged with close to 146C. Interveinal areas: Close to 155C to whiter than 155C.

*Petioles*.—Aspect: Initially upright and straight and outwardly leaning and arching with development; flexible. Length, shadehouse-grown potted plants: About 18 cm to 24 cm. Diameter, distally, shadehouse-grown potted plants: About 3.5 mm to 5 mm. Diameter, proximally, shadehouse-grown potted plants: About 6 mm to 8 mm. Texture: Smooth, glabrous. Color, shadehouse-grown potted plants: When developing and fully developed: Close to 147C and close to 147C tinged with 146C, stippled, streaked and tessellated with close to 147B; may also be tinged and flushed with close to 199B and faintly stippled, streaked and tessellated with close to 200D; distally, close to 147D tinged with close to 145D. Wing length, shadehouse-grown potted plants: About 3 cm to 5.5 cm. Wing diameter, shadehouse-grown potted plants: About 6 mm. Texture and luster, inner and outer surfaces: Smooth, glabrous; dull. Wing color, shadehouse-grown potted plants: Inner surface: Close to 155C; colors and patterns on the outer surface are visible on the inner surface. Outer surface: Close to 156D and 146D tinged with close to 199B, stippled and streaked with close to 200C and 200D.

Inflorescence description: Inflorescences observed on seven week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about seven weeks after growth commences; inflorescences last about three days before fading; inflorescences persistent.

*Spathe*.—Length, overall: About 8.7 cm. Length, distal open portion: About 6.4 cm. Length, proximal closed portion: About 2.3 cm. Width, distal open portion: About 2.7 cm. Depth, distal open portion: About 1.6 cm. Width, at constriction: About 1.5 cm. Width, proximal closed portion: About 2.4 cm. Shape, open portion: Elliptic to slightly obovate. Apex: Acuminate. Base: Acute. Margin: Entire; smooth. Texture and luster, front surface: Smooth, glabrous; dull. Texture and luster, rear surface: Smooth, glabrous; dull, proximally, slightly glaucous. Color, front surface: Distal open portion: Close to 150D; margins, close to 155C; with development, color becoming closer to 199A and N199B. Proximal closed portion: Close to 147D; color does not change with development. Color, rear surface: Distal open portion: Close to 154D; margins tinged with close to 155C; color does not change with development. Proximal closed portion: Close to 147B and 147C; random areas, close to 147D and 145D; color does not change with development.

*Spadix*.—Length, overall: About 6.6 cm. Length, male flower zone: About 4.3 cm. Length, sterile zone: About 9 mm. Length, female flower zone: About 1.4 cm. Diameter, male flower zone: About 1 cm. Diameter, sterile flower zone: About 7 mm. Diameter, female flower zone: About 1 cm. Shape: Columnar, spindle-shaped. Apex: Acute. Base: Truncate. Aspect: Upright. Color, mature, male zone: Close to 145C and 145D. Color, mature, sterile zone: Close to N155C to N155D. Color, mature, female zone: Close to 159D and N170D. Male flowers: Quantity per spadix: About 180. Shape: Obovate. Height: About 2 mm to 3 mm. Diameter: About 2.5 mm to 3 mm. Pollen amount: Abundant. Pollen color: Close to 4D. Female flowers: Quantity per spadix: About 108. Shape: Obovate. Height: About 2.5 mm. Diameter: About 1.8 mm to 2.2 mm. Stigma color: Close to 159D. Ovary color: Close to N170D.

*Scape*.—Length: About 16.5 cm. Diameter: About 5 mm. Strength: Sturdy; flexible. Aspect: Mostly erect. Texture and luster: Smooth, glabrous; dull sheen. Color: Close to 147C and close to 147C tinged with close to 146C and faintly stippled, streaked and tessellated with close to 147B; distally, close to 147D tinged with close to 146D.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WWG 2320-373' as illustrated and described.

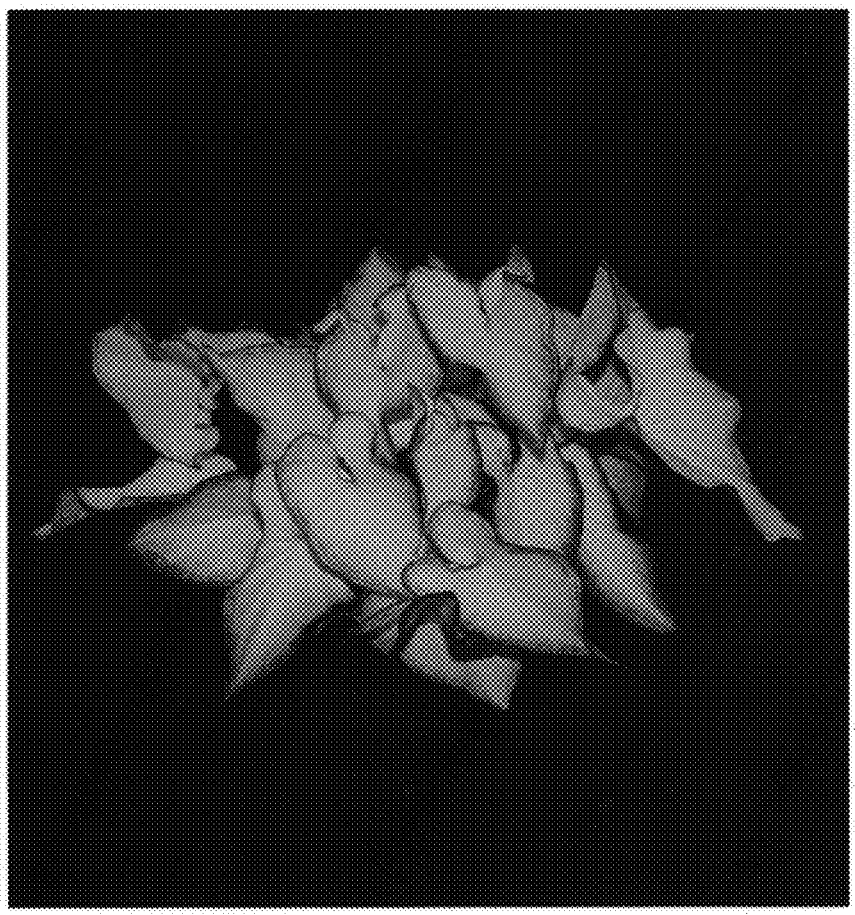

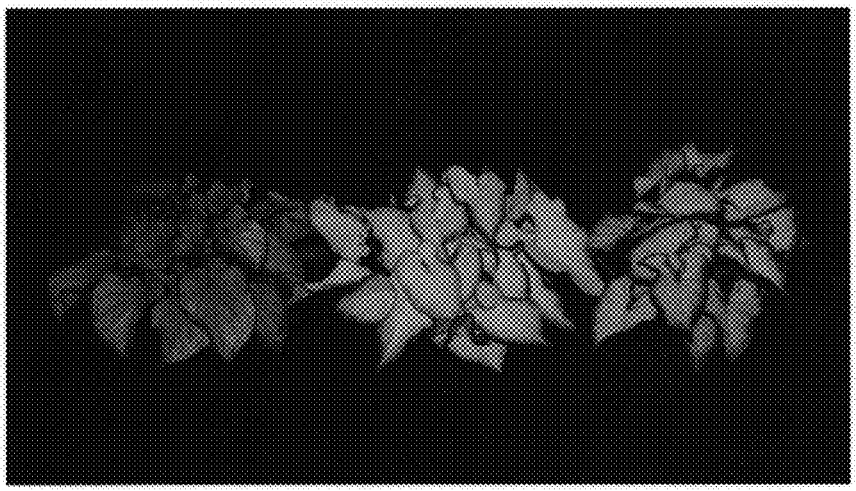
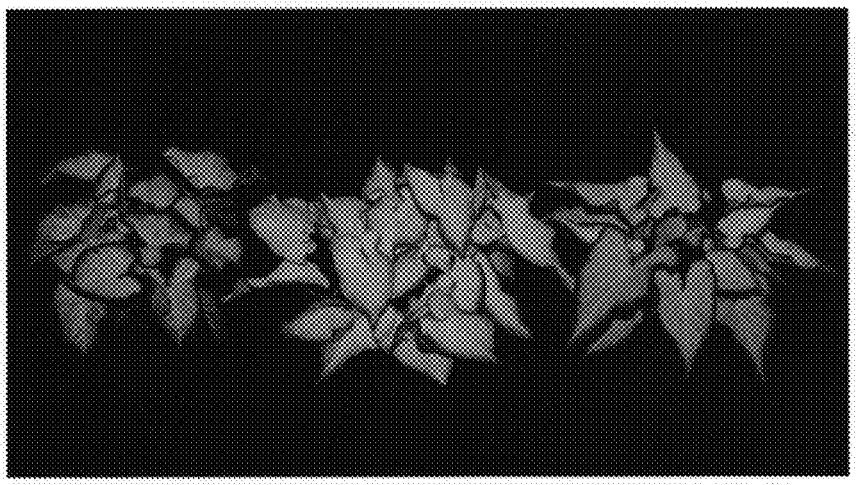

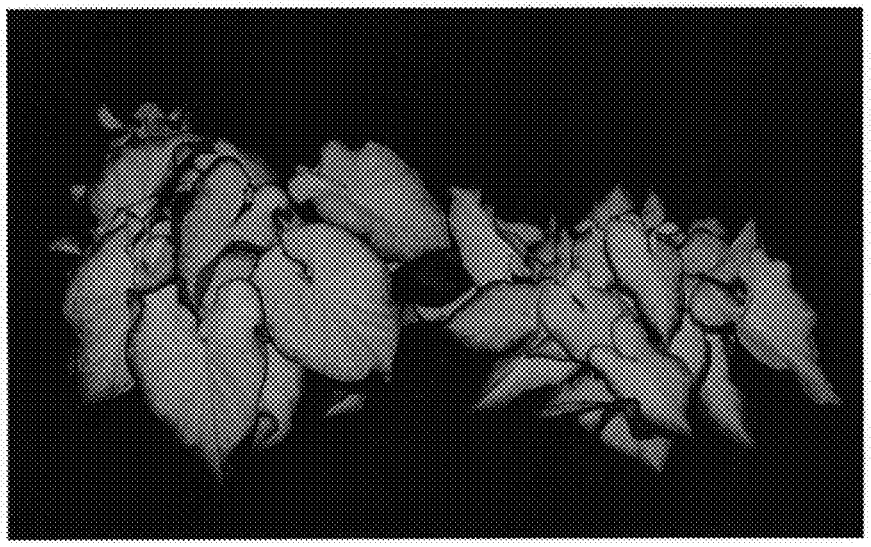
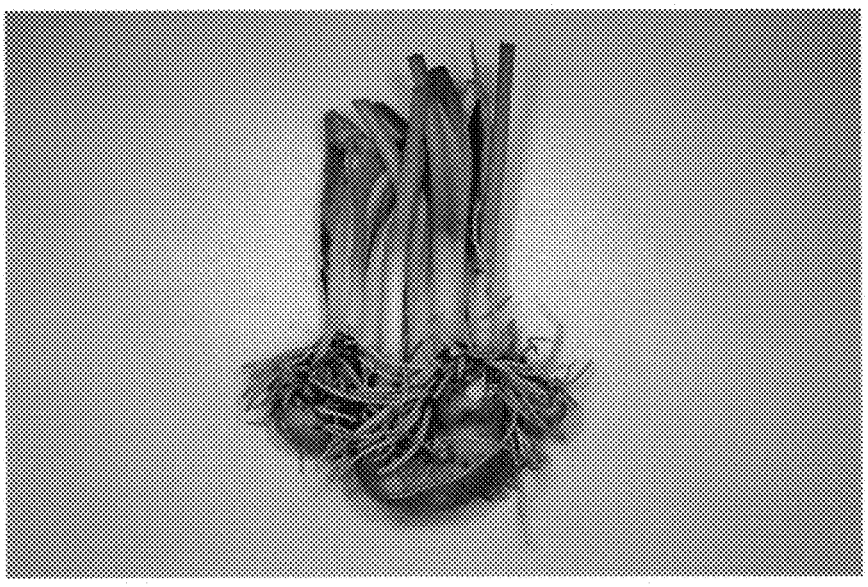

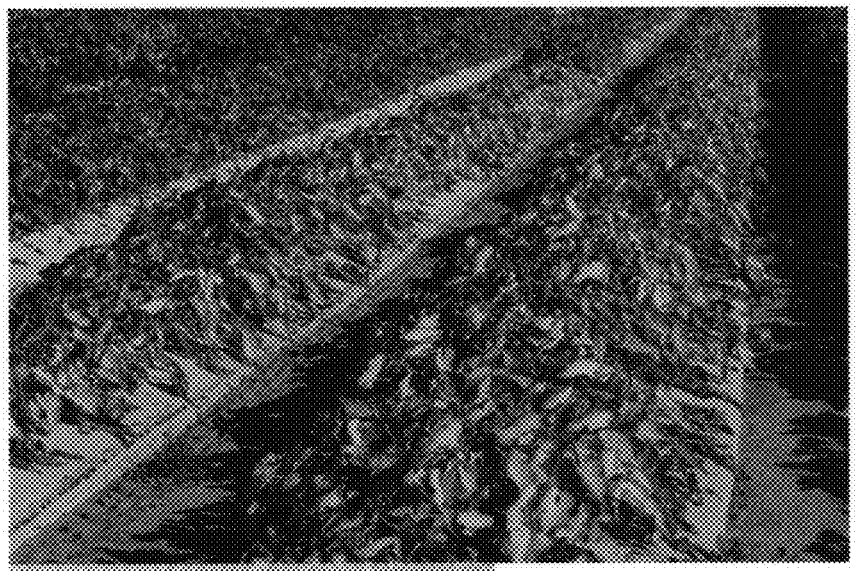
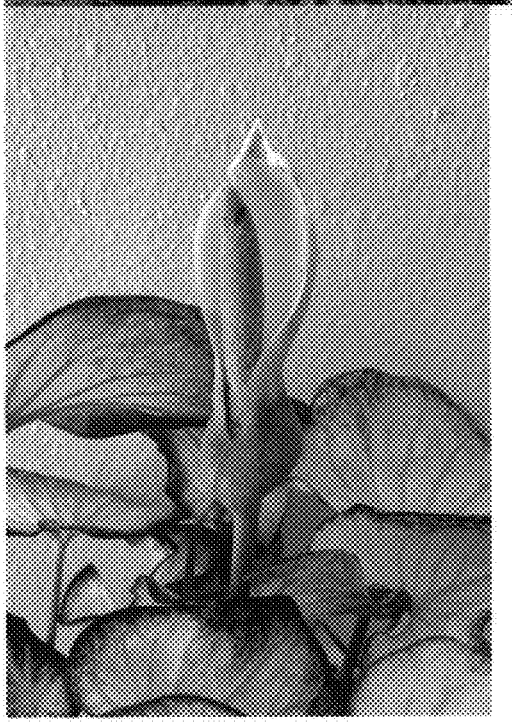

* * * * *